(12) United States Patent
Kane et al.

(10) Patent No.: US 6,277,070 B1
(45) Date of Patent: Aug. 21, 2001

(54) MEDICAL ANALYSIS AND TREATMENT METHOD AND SYSTEM

(75) Inventors: Edward Kane; Patricia C. Kane; Raymond A. Skinner, all of Millville, NJ (US)

(73) Assignee: Body Bio Corporation, Millville, NJ (US)

( * ) Notice: Subject to any disclaimer, the term of this patent is extended or adjusted under 35 U.S.C. 154(b) by 0 days.

(21) Appl. No.: 09/305,724

(22) Filed: May 5, 1999

Related U.S. Application Data

(63) Continuation-in-part of application No. 09/072,603, filed on May 5, 1998.

(51) Int. Cl.[7] .................................................. A61B 5/00
(52) U.S. Cl. ............................................................. 600/300
(58) Field of Search .................................... 600/300, 301

(56) References Cited

U.S. PATENT DOCUMENTS

| | | | |
|---|---|---|---|
| 4,290,114 | 9/1981 | Sinay | 364/900 |
| 4,731,725 | 3/1988 | Suto et al. | 364/415 |
| 4,733,354 | 3/1988 | Potter et al. | 364/415 |
| 5,023,785 | 6/1991 | Adrion et al. | 364/413.08 |
| 5,075,101 | 12/1991 | Siguel | 424/9 |
| 5,255,187 | 10/1993 | Sorensen | 364/413.02 |
| 5,315,505 | 5/1994 | Pratt et al. | 364/633.01 |
| 5,437,278 | 8/1995 | Wilk | 128/653.1 |
| 5,463,548 | 10/1995 | Asada et al. | 364/413.02 |
| 5,594,638 | 1/1997 | Iliff | 395/203 |
| 5,642,731 | 7/1997 | Kehr | 128/630 |
| 5,704,350 | 1/1998 | Williams, III | 128/630 |
| 5,967,994 | * 10/1999 | Wang | 600/509 |

FOREIGN PATENT DOCUMENTS

WO 97/20496 * 6/1997 (WO) .................................. 600/300

* cited by examiner

*Primary Examiner*—Robert L. Nasser
(74) *Attorney, Agent, or Firm*—Drinker Biddle & Reath LLP

(57) ABSTRACT

The present invention provides a system and method for medical analysis treatment. The system includes a computer system for storing a plurality of databases. The databases maintain medical research data regarding analyte characteristics and vitamin/nutrient characteristics. A first database maintains a plurality of analyte records, wherein each record holds information regarding a particular analyte that was determined from the results of testing a human test group. Each analyte record includes a low value, a high value and a target value. A second database maintains a plurality of vitamin/nutrient records wherein each vitamin/nutrient record includes analytes associated with the particular vitamin/nutrient and an analyte level indicative of vitamin/ nutrient that may have supportive effect. The method matches an individual's bodily fluid laboratory results with the databases to identify supportive nutrient metabolic agents for each of the analytes within a lab report, potential negative drug reaction to each analyte as they pertain to the individual's analyte status.

41 Claims, 15 Drawing Sheets

BASIC STATUS REPORT
FATTY ACID RED CELL MEMBRANE DATE:

PATIENT ID:

THE % STATUS IS THE WEIGHTED DEVIATION OF THE LABORATORY RESULT.

LOW RESULTS

| | %STATUS | | RESULT | LOW | HIGH |
|---|---|---|---|---|---|
| 18:0 DMA | −129.55 | L | 1.66 | 2.01 | 2.45 |
| GONDOIC C20:1W9 | −116.67 | L | 0.03 | 0.11 | 0.23 |
| 16DMA | −90.00 | L | 0.91 | 1.03 | 1.33 |
| TRANSVACCENIC C18:1W7t | −64.89 | L | 0.29 | 0.43 | 1.37 |
| PENTACOSANOIC C25:0 | −60.00 | L | 0.02 | 0.03 | 0.13 |
| ARACHIDONIC C20:4W6 | −51.56 | L | 12.48 | 12.51 | 14.43 |
| EICOSAPENTA. C20:5W3 | −42.86 | L | 0.33 | 0.29 | 0.85 |
| DOCOSAHEXA. C22:6W3 | −42.67 | L | 3.07 | 2.90 | 5.22 |
| CAPROLEIC C10:1 | −33.33 | L | 0.01 | 0.00 | 0.06 |
| DOCOSAPENTA. C22:5W6 | −31.48 | L | 0.53 | 0.43 | 0.97 |
| PALMITOLEIC C16:1W7 | −30.00 | L | 0.31 | 0.25 | 0.55 |
| 18:1 DMA | −28.05 | L | 0.32 | 0.14 | 0.96 |

FIG. 4B

BASIC STATUS REPORT

PATIENT ID:

PRACTITIONER:

BLOOD TEST DATE:

THE % STATUS IS THE WEIGHTED DEVIATION OF THE LABORATORY RESULT.

| | %STATUS | | RESULT | LOW | HIGH |
|---|---|---|---|---|---|
| A/G RATIO | 30.00 | H | 1.76 | 0.80 | 2.00 |
| ALBUMIN | -13.16 | | 4.40 | 3.70 | 5.60 |
| ALKALINE PHOSPHATASE | -26.46 | L | 223.00 | 130.00 | 525.00 |
| ANION GAP | 43.00 | H | 19.30 | 10.00 | 20.00 |
| B.U.N. | -33.33 | L | 10.00 | 8.00 | 20.00 |
| B.U.N./CREATININE RATIO | -28.95 | L | 10.00 | 6.00 | 25.00 |
| BASOPHIL COUNT | -26.00 | L | 48.00 | 0.00 | 200.00 |
| BASOPHILS | 0.00 | | 1.00 | 0.00 | 2.00 |
| BILIRUBIN, TOTAL | -25.00 | L | 0.50 | 0.20 | 1.40 |
| CALCIUM | -10.00 | | 9.80 | 9.20 | 10.70 |
| CALCIUM/PHOSPHORUS RATIO | -8.48 | | 2.13 | 1.30 | 3.30 |
| CHLORIDE | 25.00 | H | 106.00 | 100.00 | 108.00 |
| CHOLESTEROL | -2.45 | | 165.00 | 97.00 | 240.00 |
| CO2 | -83.33 | L | 22.00 | 24.00 | 30.00 |
| CREATININE | 16.67 | | 1.00 | 0.60 | 1.20 |
| EOSINOPHIL COUNT | -2.00 | | 240.00 | 0.00 | 500.00 |
| EOSINOPHILS | 50.00 | H | 5.00 | 0.00 | 5.00 |
| FREE T4 INDEX (T7) | -37.50 | L | 1.40 | 1.05 | 3.85 |
| GGT | 159.52 | H | 56.00 | 12.00 | 33.00 |
| GLOBULIN | -12.50 | | 2.50 | 1.90 | 3.50 |
| GLUCOSE | -9.52 | | 91.00 | 74.00 | 116.00 |
| HDL | -33.33 | L | 40.00 | 35.00 | 65.00 |
| HEMATOCRIT | -27.42 | L | 44.30 | 42.90 | 49.10 |
| HEMOGLOBIN | 0.00 | | 15.50 | 14.40 | 16.60 |
| IRON, TOTAL | -22.64 | | 57.00 | 28.00 | 134.00 |

FIG. 4C

PATIENT ID:

BASIC STATUS REPORT

BLOOD TEST DATE:

THE % STATUS IS THE WEIGHTED DEVIATION OF THE LABORATORY RESULT.

LOW RESULTS

| | %STATUS | | RESULT | LOW | HIGH |
|---|---|---|---|---|---|
| CO2 | −83.33 | L | 22.00 | 24.00 | 30.00 |
| THYROXINE (T4) | −48.65 | L | 5.10 | 5.00 | 12.40 |
| W.B.C. | −46.47 | L | 4.80 | 4.50 | 13.00 |
| NEUTROPHIL COUNT | −44.97 | L | 2112.00 | 1800.00 | 8000.00 |
| NEUTROPHILS | −42.59 | L | 44.00 | 42.00 | 69.00 |
| SGPT | −41.43 | L | 13.00 | 10.00 | 45.00 |
| FREE T4 INDEX (T7) | −37.50 | L | 1.40 | 1.05 | 3.85 |
| R.B.C. | −36.84 | L | 4.83 | 4.73 | 5.49 |
| B.U.N. | −33.33 | L | 10.00 | 8.00 | 20.00 |
| HDL | −33.33 | L | 40.00 | 35.00 | 65.00 |
| SGOT | −30.00 | L | 20.00 | 15.00 | 40.00 |
| LDH | −29.41 | L | 155.00 | 120.00 | 290.00 |
| LYMPHOCYTE COUNT | −29.13 | L | 2160.00 | 1200.00 | 5800.00 |
| B.U.N./CREATININE RATIO | −28.95 | L | 10.00 | 6.00 | 25.00 |
| HEMATOCRIT | −27.42 | L | 44.30 | 42.90 | 49.10 |
| ULTRA-SENSITIVE TSH | −27.08 | L | 1.40 | 0.30 | 5.10 |
| ALKALINE PHOSPHATASE | −26.46 | L | 223.00 | 130.00 | 525.00 |
| BASOPHIL COUNT | −26.00 | L | 48.00 | 0.00 | 200.00 |
| BILIRUBIN, TOTAL | −25.00 | L | 0.50 | 0.20 | 1.40 |

FIG. 4D

MEDICAL ANALYSIS AND TREATMENT METHOD AND SYSTEM

CROSS-REFERENCE TO RELATED APPLICATION

This is a continuation-in-part of copending application Ser. No. 09/072,603, filed May 5, 1998.

FIELD OF THE INVENTION

The present invention relates generally to automated medical analysis and treatment systems and methods for performing medical analysis, and more particularly to such systems and methods that compare patient diagnostic data with predetermined ranges of specific analyte values to provide suggested or contraindicated treatment strategies.

BACKGROUND OF THE INVENTION

Medical research in the second half of the 20th century has produced, and continues to produce, an ever increasing body of knowledge. The complexity and interrelationships of various diseases and the analytes that may be detected in various diagnostic tests for diseases are more than sufficient to tax the capacity of most medical practitioners. To aid medical practitioners in disease diagnosis, computerized expert systems have been developed to collate medical diagnostic data with various diseases to guide physicians in prescribing treatments for their patients. Such prior art medical diagnostic systems do not adequately provide a framework for analyzing the individual patient's diagnostic results to collate such results into a disease analyte pattern. Furthermore, such systems do not address therapeutic and/or contraindicated treatment strategies.

One method, described in PCT Publication Number WO 97/20496, uses the mean value of human experience test results to determine a presence level of a particular indicator for an individual. The use of the mean value does not provide an accurate determination of whether an individual's indicator levels are within a normal range.

An individual's metabolism is determined, at least in part, by the amount of raw materials available to the individual and the concentration of enzymes available to the individual to work on the raw materials. The amount of raw materials present in the individual can be determined by measuring the individual's fatty acids. Furthermore, the concentration of enzymes present in the individual can be determined by measuring various elements of the individual's blood. As such, an individual's body chemistry can be used to provide recommendations to improve metabolism. It is known to analyze an individual's fatty acids to diagnose the individual's health. Furthermore, it is known to analyze an individual's blood or other bodily fluids to diagnose the individual's health. However, it is neither known nor suggested in the state of the art to use both conventional blood testing techniques and a red cell membrane fatty acid test to measure deficiencies in the individual's raw materials and enzymes and therein generate a comprehensive regimen of vitamins and/or nutrients that provide favorable effects on the individual's health.

SUMMARY OF THE INVENTION

The present invention is a computerized medical analysis, diagnosis, and treatment system and method. The system and method are used to analyze and diagnose an individual's analyte levels. An "analyte" is any substance that is quantified or detected by an experimental procedure. The present invention provides a method for identifying supportive nutrients and/or vitamins based upon a comparison between the concentration of the analytes in the individual and the concentration of the analyte found in a test group. "Supportive nutrients and/or vitamins" are those nutrients and/or vitamins that have favorable effects on the amount of a particular analyte in the individual. In order to carry out the method of the present invention and thereby perform the analysis and diagnosis and provide a treatment recommendation, the individual is tested to determine an analyte value for the various analytes found in their body. The test may be performed through various methods, such as through drawing and testing blood, urine or other bodily fluids. The results of the testing provide analyte values for each of the analytes for the individual. In a preferred embodiment of the present invention the individual's blood is drawn and the red blood cell membranes are tested in a conventional manner to those skill in the art for a panel of fatty acid analytes. Also in the preferred embodiment of the present invention the individual's blood is drawn and tested in a conventional manner to those skilled in the art for a panel of non-fatty acid analytes.

The system of the present invention, as illustrated in FIG. 1, includes a computer 100 including at least a central processing unit (CPU) 102 and a storage medium 104. The storage medium 104 may be, for example, a hard disk drive. The system may also include an input device 106, for example a keyboard, a mouse or a disk drive and an output device 108, for example a monitor or a printer. The system includes a first database stored on the storage medium. The first database maintains analyte data information, in the form of analyte values, for a plurality of analytes. The first database information is organized in a plurality of analyte records, wherein each record holds information regarding a particular analyte that was determined from the results of testing a human test group in the same manner the individual was tested to determine the individual's analyte values. Each analyte record includes an analyte low value, an analyte high value and an analyte target value. The system also includes a second database stored on the storage medium. The second database maintains vitamin/nutrient information, including a group of vitamin/nutrients and associated analytes, for the group of vitamins/nutrients. The second database information is organized in a plurality of vitamin/nutrient records, wherein each record holds information regarding a particular vitamin/nutrient. Each vitamin/nutrient record includes a set of analytes associated with that particular vitamin/nutrient. Each analyte of the analyte set has an associated analyte level. The analyte level is indicative of an effect the particular vitamin/nutrient has on the associated analytes. Once the databases are stored on the storage medium, an individual's analyte values are then input to the CPU and compared with the first database data to determine a presence levels for each analyte for the individual. The presence level is the relative amount of a particular analyte present in the individual in comparison to the human test group. Thereafter the presence levels are compared with the second database data to determine a group of vitamins/nutrients that has supportive effects of the patient analyte levels.

The present invention further provides an automated medical diagnostic database system wherein the known effects of various drugs and other nutritional-biochemical elements can be utilized to better analyze an individuals health status, and to identify therapeutic and/or contraindicated drugs and elements.

These and other features and advantages of the present invention will become well understood upon reading the following detailed description of the invention.

DESCRIPTION OF THE INVENTION

Figure 1:
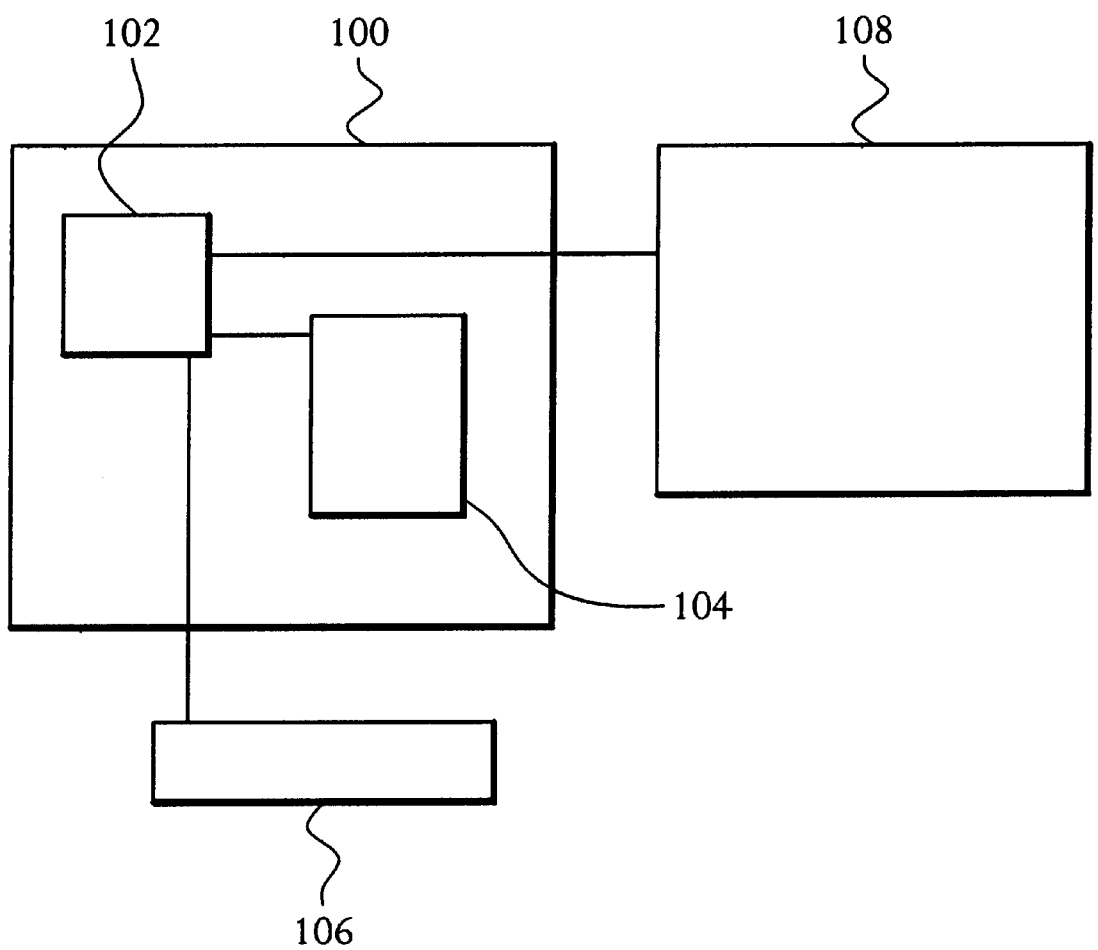
FIG. 1 is a block diagram illustrating the basic system of the present invention.

The system of the present invention may be implemented through hardware, software or any combination of the two. As illustrated in FIG. 1, the system of the present invention includes a computer 100 housing a CPU 102 and a storage medium 104, also known as a memory device. The system may operate under control of a control program or application written to implement the method of the present invention. The control program includes source code instructions that direct the operation of the CPU 102 and the other elements of the system. The control program may be stored in the memory device 104 or the CPU 102.

The method of the present invention involves the analysis of an individual's analyte values, obtained from testing the individual's blood or other bodily fluids to determine the analyte presence level for each of the individual's analytes and then compare the individual's analyte presence levels with a set of known analyte presence levels for various vitamins/nutrients to determine a group of supportive vitamins/nutrients for an individual in light of the analyte presence levels. The method is basically accomplished in six steps which are depicted in FIG. 2 and described below.

Figure 2:
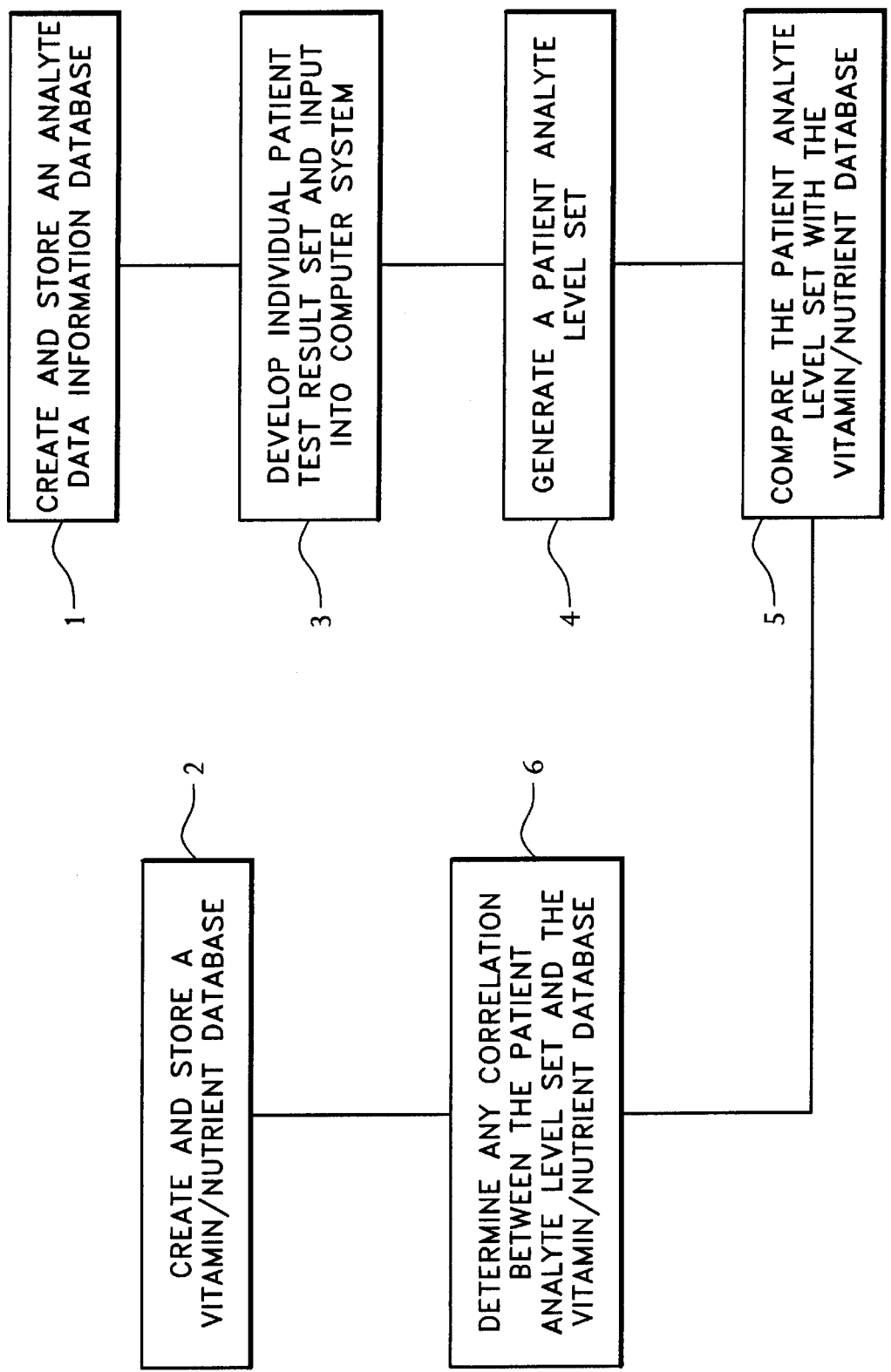
FIG. 2 is a block diagram illustrating the basic method of the present invention.
Figure 4A:
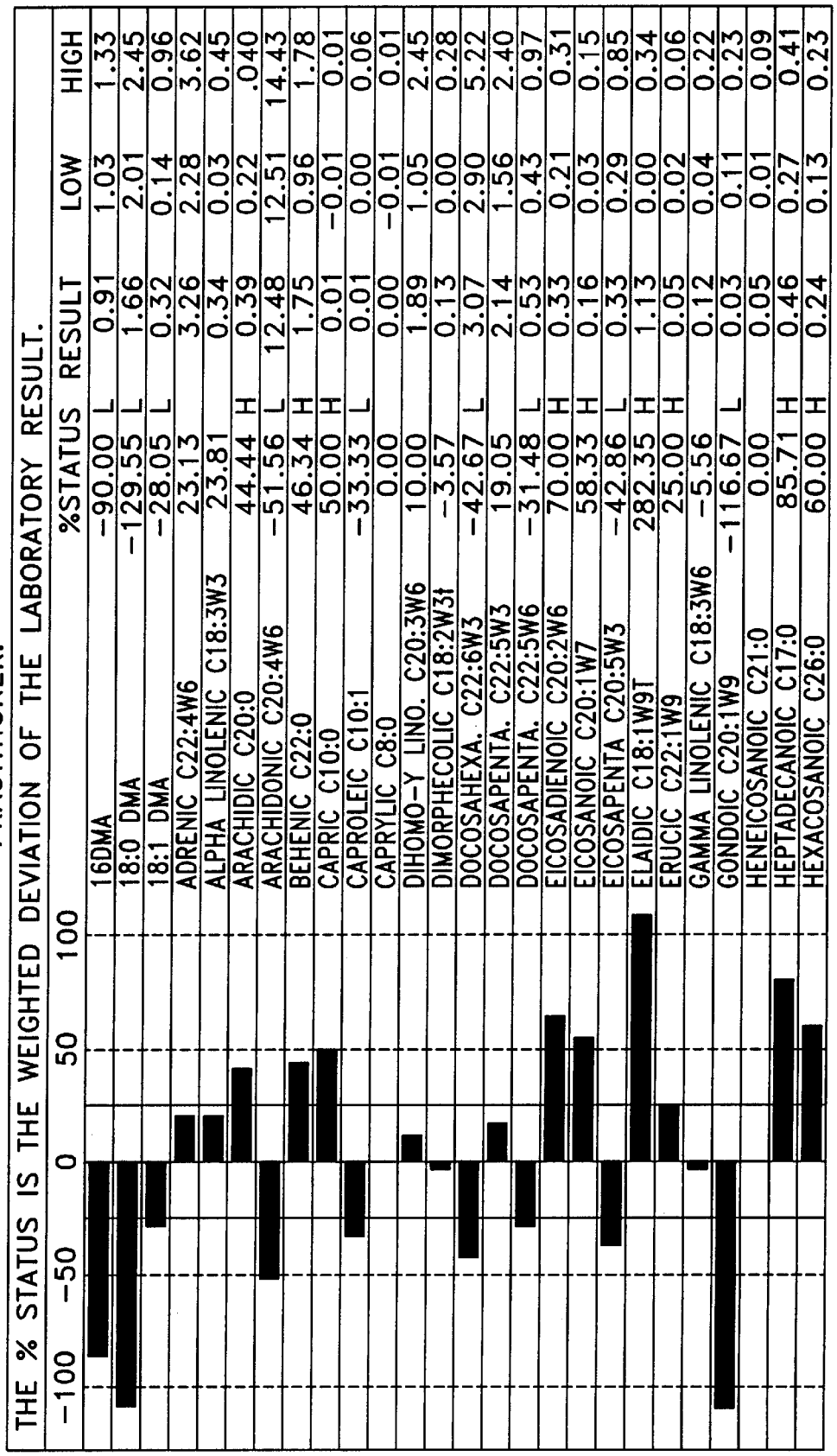
FIGS. 4A–4D are examples of basic status reports generated by the present invention.
Figure 4A:
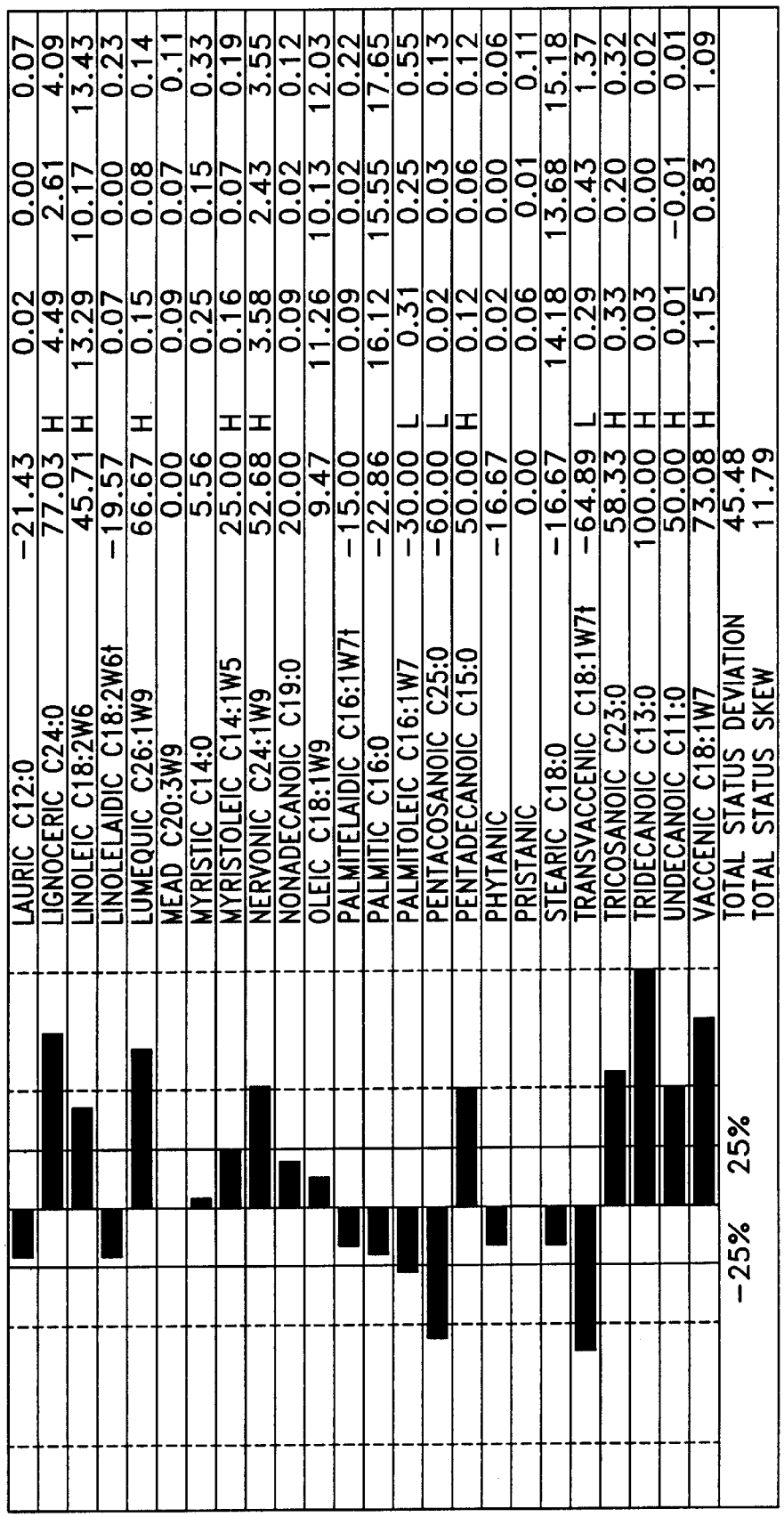
Figure 4B:
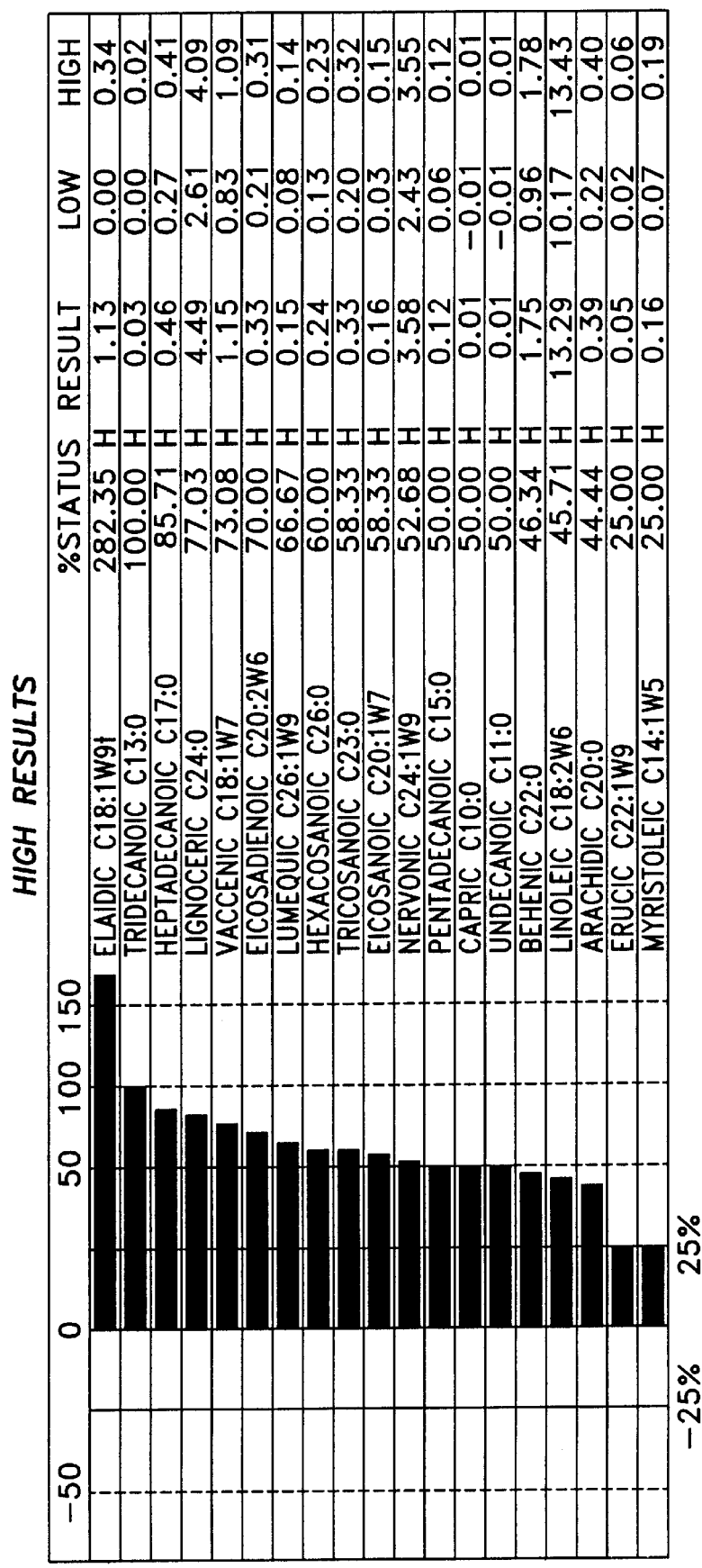

FIG. 2 is a block diagram setting forth the various steps in the analytical disease indication method of the present invention. In step 1, a first database is created and stored in a storage medium. The first database maintains analyte data information for a plurality of analytes determined from a statistical analysis of analyte values obtained through testing a human test group, as described above. Each of the subjects of the test group are screened for a particular set of analytes. For example, each subject is screened for a set of fatty acid analytes and a set of non-fatty acid analytes. A value representative of the amount of each of the fatty acid analytes and the non-fatty acid analytes is determined and becomes part of the statistical analysis. The fatty acid analyte values may be obtained by drawing a blood sample from each subject and conducting a conventional fatty acid red cell membrane test known to those skilled in the art on the sample. The non-fatty acid analyte values may be obtained by drawing another blood sample from each subject and conducting a conventional blood chemistry test known to those skilled in the art on the sample. A listing of the fatty acid analytes detected by the fatty acid red cell membrane test are illustrated in FIGS. 4A and 4B. The first database maintains an analyte record for each of those analytes.

With regard to FIG. 4A, the acronym "DMA" stands for dimethylacetyl. In addition, the code following the listed fatty acids defines the number of carbon atoms in the acid and the number and location of any double bonds. For example, "Adrenic C22:4ω6" denotes adrenic acid, having twenty-two carbon atoms with four double bonds, the first of which is located at the sixth carbon atom from the omega or tail end of the carbon chain.

Figure 4C:
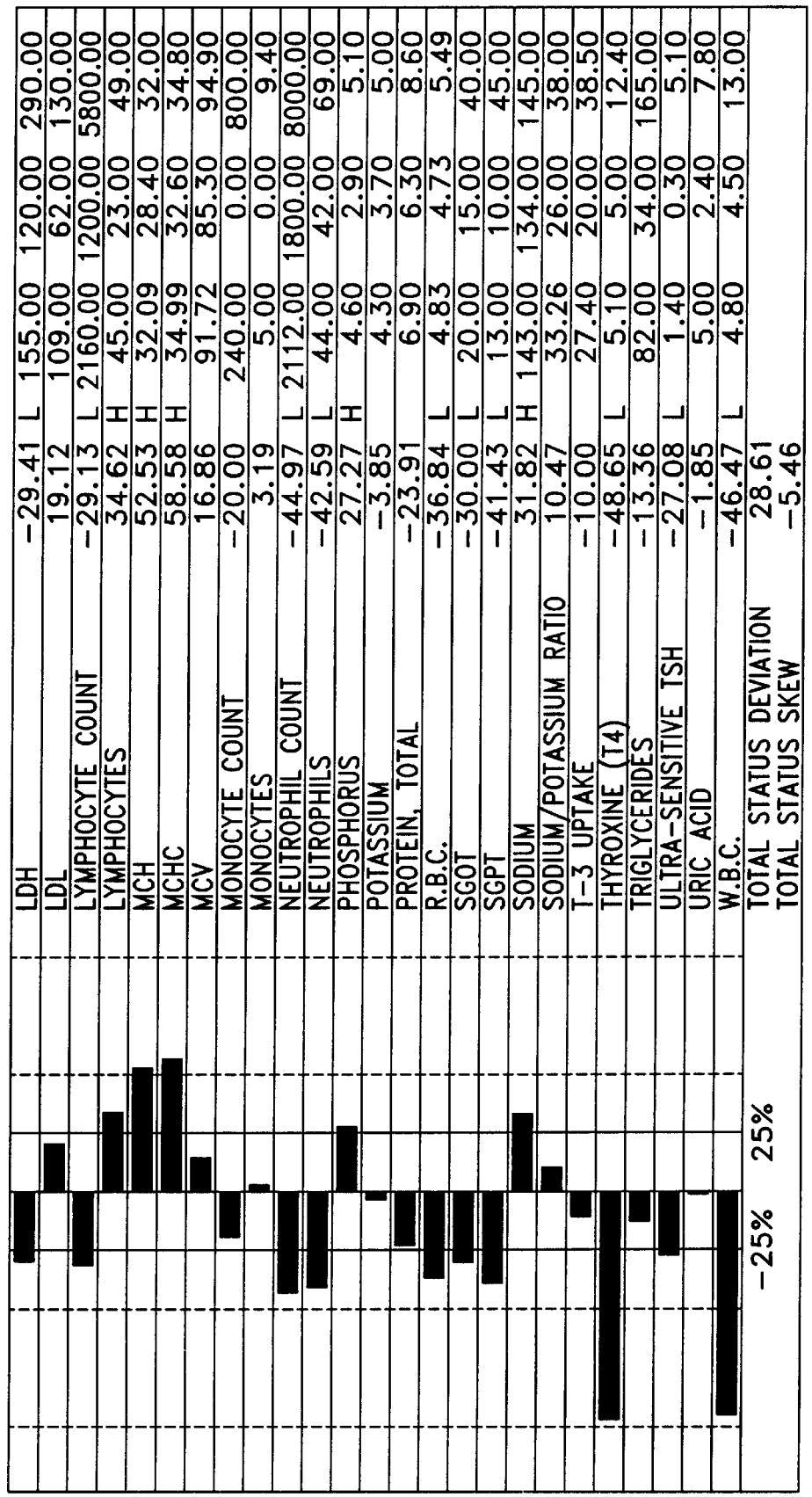
Figure 4D:
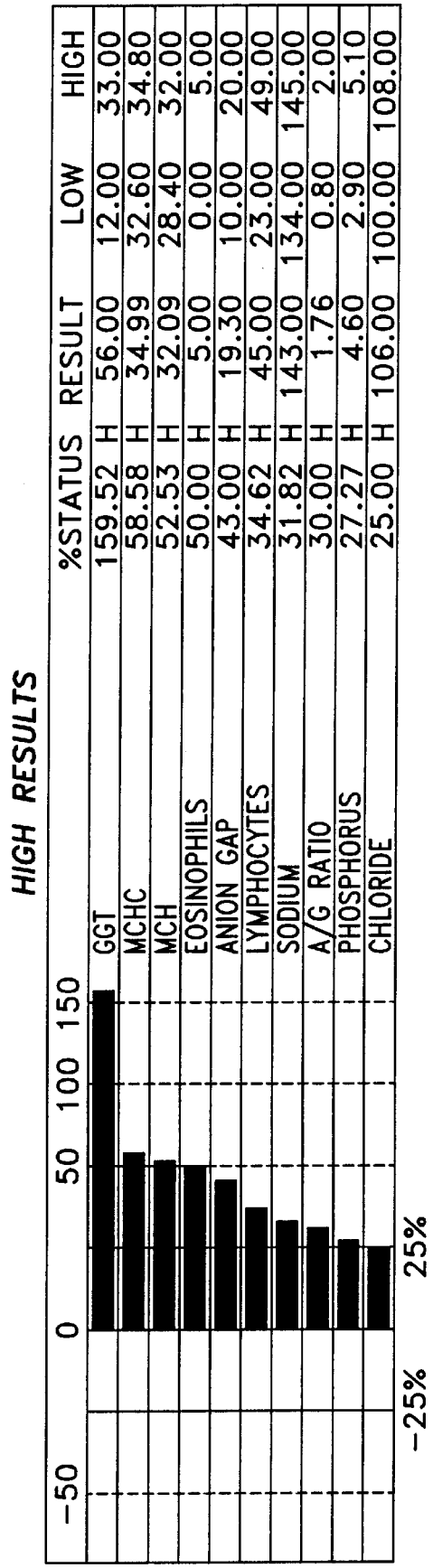

A listing of the non-fatty acid analytes detected by the blood chemistry test are illustrated in FIGS. 4C and 4D. The first database also maintains an analyte record for each of those analytes.

Figure 3A:
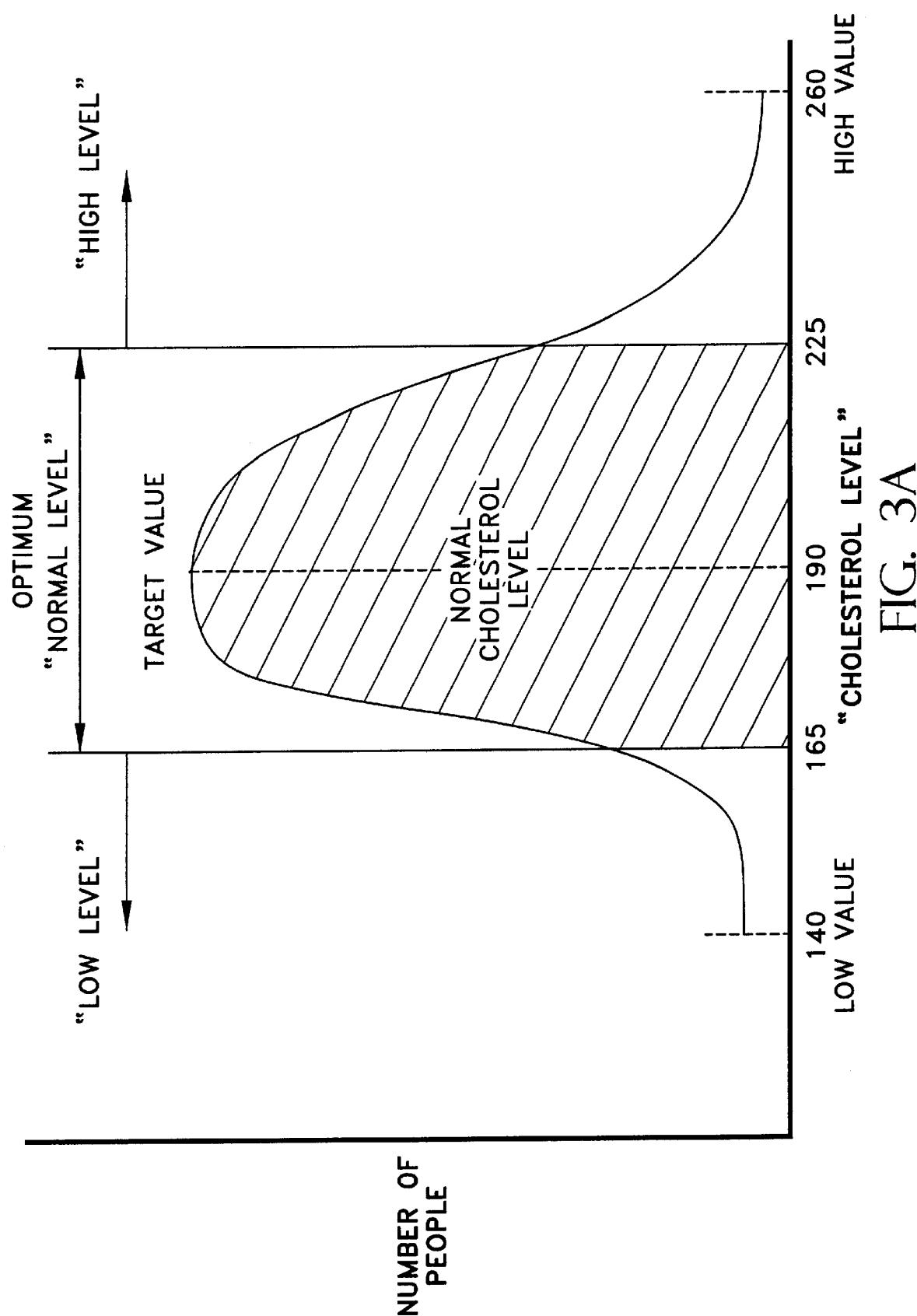
FIGS. 3A and 3B are a graph illustrating a manner in which High, Low and Normal levels of an analyte are determined in conjunction with the present invention.

Table 1 is representative of the first database. In a preferred embodiment, the first database includes an analyte low value, an analyte high value and an analyte target value for each analyte. An "analyte target value" is that value of a curve frequency distribution which is considered the healthiest value for a human being and therefore represents the value an individual's analyte levels should be driven towards. Different curve shapes determine what is considered the healthiest value or target value. For example, the plot illustrated in FIG. 3A shows a statistical analysis for a particular analyte, cholesterol in this example. This plot is representative of the analyte values obtained from the human test group for the analyte cholesterol. The horizontal axis indicates the cholesterol value. The vertical axis the number of individuals in the human test group that had a particular cholesterol value. In this example, the high value is 260 and the low value is 140. In a curve having this shape type or one similar to it, the mode value (190 in this case) is used as the target value. The high and low values are determined as two standard deviations of the results generated from the human test group for the particular analyte, in this instance, cholesterol. The mode value is the analyte value that has the greatest number of people from the human test group with that value. In other words, the mode value is the analyte value at the highest point of the curve representative the results from the human test group for a particular analyte. In this instance the mode value is considered the optimum value for an individual. Therefore, the practitioner will act to drive the individual's analyte values to the mode value. In order to drive the individual's analyte values to the mode value, the practitioner must be able to work from an individual's analyte levels that are a function of the mode value. The present invention provides the system and method for providing analyte levels of this type. This is discussed in more detail below.

TABLE 1

| ANALYTE | LOW VALUE | HIGH VALUE | MODE VALUE |
| --- | --- | --- | --- |
| 1 | 25 | 150 | 90 |
| 2 | 5 | 26 | 14 |
| 3 | 8.5 | 10.8 | 9.6 |
| 4 | 96 | 109 | 103 |
| 5 | 1.9 | 3.5 | 2.6 |
| 6 | 3.90 | 9.0 | 4.7 |
| 7 | 0 | 240 | 170 |
| 8 | 3.3 | 4.5 | 3.5 |
| 9 | 140 | 260 | 190 |
| . | . | . | . |
| . | . | . | . |
| . | . | . | . |

Figure 3B:
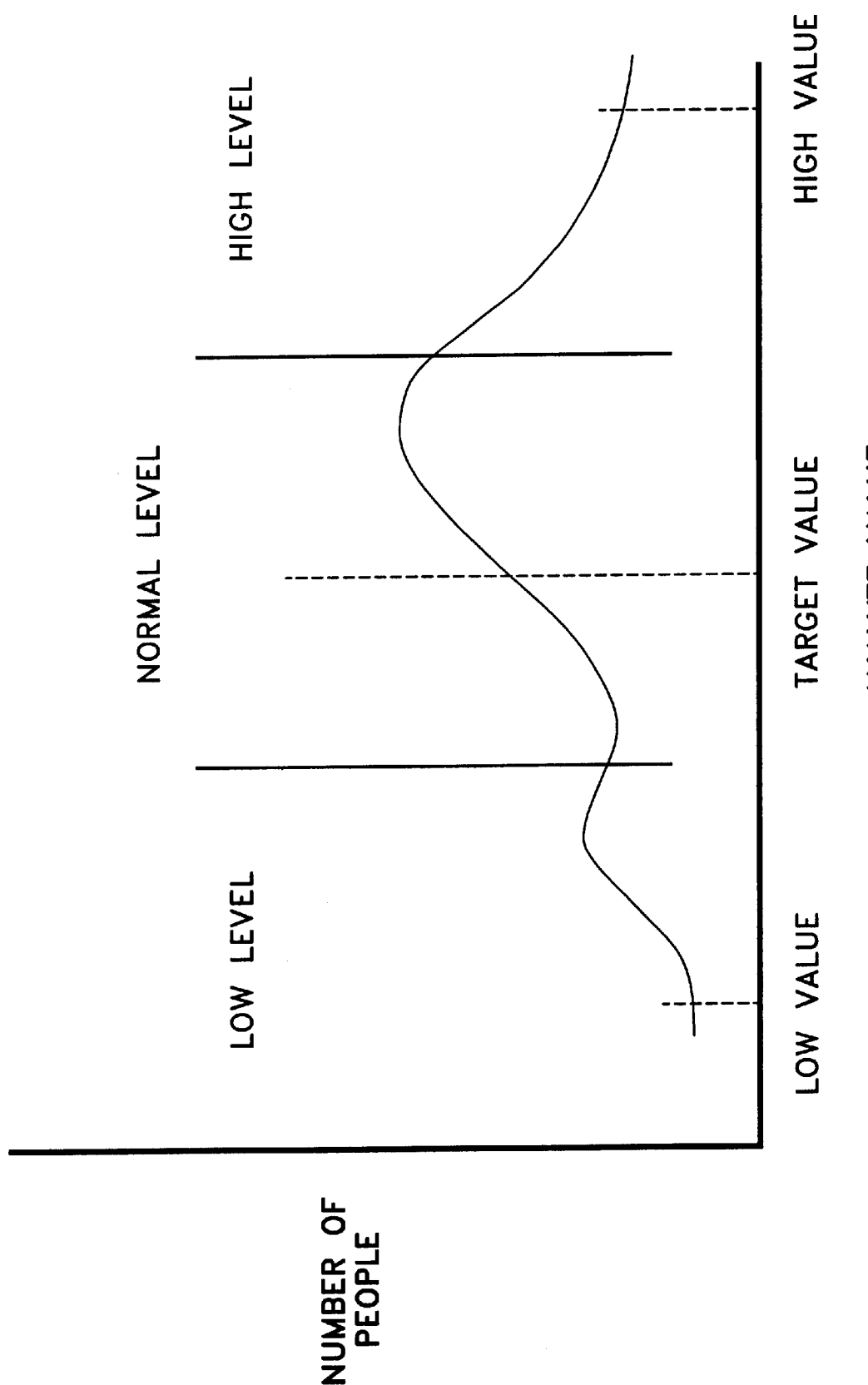

In a different situation, the target value may be a weighted average value of the values in the frequency distribution for the particular analyte. Referring to FIG. 3B, the plot shows another example of a statistical analysis for an analyte.

Similar to FIG. 3A, the horizontal axis indicates the analyte value and the vertical axis indicates the number of individuals in the human test group that had a particular analyte value. Through the generation of these plots and the development of the frequency distribution, it has been discovered that some analytes present curves in which the mode is not the healthiest point. In these types of curves, the weighted average value is considered the healthiest point and therefore used as the target value.

Referring again to FIG. 2, in step 2 a second database is created and stored in the storage medium. The second database maintains data information regarding a plurality of vitamins and nutrients. Table 2 is representative of the second database. In a preferred embodiment, the second database includes a vitamin/nutrient record for each of the plurality of vitamins and nutrients. Each particular vitamin/nutrient record also includes a set of analytes upon which the particular vitamin or nutrient has a supportive effect. By supportive effect, it is meant that the vitamin or nutrient drives a particular analyte towards the normal range. For instance, if an individual's particular analyte value has been determined to fall within the HIGH range, than the vitamin or nutrient that has that analyte in its database record will drive the analyte level lower and towards the NORMAL range. To this end, once the individual's analyte level set has been generated, it can be compared to the vitamin/nutrient database. This comparison will provide a group of nutrients and/or vitamins that can be prescribed to the individual to drive the analyte levels towards the normal. Table 2 is an example of a chart indicating recommended vitamins and/or nutrients for a vitamin/nutrient database for HIGH, LOW and NORMAL analyte levels. The database includes a plurality of vitamins and nutrients, for example Acetic Acid. The vitamin or nutrient has analytes associated with it correlated with an analyte level. The database indicates the particular vitamins or nutrients that are suggested to drive an out of normal range analyte level towards the normal range. As shown, Acetic Acid is suggested for a HIGH and/or NORMAL calcium level and a HIGH sodium level.

The present invention also provides for method for identifying vitamins and/or nutrients for an individual whose analyte values suggest a minor imbalance. By minor imbalance it is meant that the percent status values fall between 12.5 and 25 or between −12.5 and −25. To this end, the percent status values may be input to the CPU and compared to the vitamin/nutrient database to determine the vitamins and/or nutrients that would drive the individual's analyte values towards the mode value.

TABLE 2

| Low | Normal | High |
|---|---|---|
| Abalone | | |
| Cholesterol | Cholesterol | Eosinophils |
| $CO_2$ | $CO_2$ | |
| GGT | Eosinophils | |
| Potassium | GGT | |
| Sodium | Potassium | |
| | Sodium | |
| Acetic Acid | | |
| | Calcium | Calcium |
| | | Sodium |
| Acetyl Carnitine | | |
| W.B.C | | Cholesterol |
| | | Triglycerides |
| | | W.B.C. |
| Acorn Squash | | |
| Calcium | Calcium | |
| GGT | GGT | |
| Adenosylcobalamin | | |
| Phytanic | | Lignoceric C24:0 |
| Pristanic | | Phytanic |
| | | Phytanic |
| Advera | | |
| Uric Acid | B.U.N. | Protein, Total |

Table 3 presents a typical tabulation of some known analytes with test results to provide added understanding by way of specific example. These test results and human experience high, low and target values are derived from known medical research, and step 2 thus comprises a database of known medical research. As stated above, the target value may be either a mode value or a weighted average value, dependent upon the curve type.

TABLE 3

| ANALYTE | RESULT | LOW VALUE | HIGH VALUE | TARGET VALUE | % STATUS | PRESENCE LEVEL |
|---|---|---|---|---|---|---|
| 1. Alkaline Phosphatase | 68 | 25 | 150 | 90 | −17 | N |
| 2. B.U.N. | 9 | 5 | 26 | 14 | −21 | N |
| 3. Calcium | 9.3 | 8.5 | 10.8 | 9.6 | −14 | N |
| 4. Chloride | 108 | 96 | 109 | 103 | 42 | H |
| 5. Globulin | 2.0 | 1.9 | 3.5 | 2.6 | −43 | L |
| 6. Uric Acid | 6.0 | 3.9 | 9.0 | 4.7 | 15 | N |
| 7. Lactate Dehydrodenase | 222 | 0 | 240 | 170 | 37 | H |
| 8. Phosphorus | 3.3 | 2.5 | 4.5 | 3.5 | −10 | N |
| 9. Cholesterol | 160 | 140 | 260 | 190 | −30 | L |
| . | . | . | . | . | . | . |
| . | . | . | . | . | . | . |
| . | . | . | . | . | . | . |

Referring again to FIG. 2, the particular individual's analyte values are input to the CPU, in step 3. According to the present invention, the individual's analyte values are determined from testing blood, serum, urine or other bodily fluids. The collected data may be formatted as a basic status report indicating the individual's analyte values. Examples of such basic status reports are illustrated in FIGS. 4A–4C. A patient test result set includes an analyte value for each of the plurality of analytes maintained in the first database. Each analyte value of the patient test result set is an appropriate numerical value indicative of the individual's analyte value. Table 4 illustrates an individual's patient test result set. This table contains 9 analytes. This is meant only to illustrate the set and not to limit the number of possible analytes that may be tested. The patient test result set is also included as the second column in Table 3.

TABLE 4

| PATIENT TEST RESULTS | | | | | | | | | |
|---|---|---|---|---|---|---|---|---|---|
| ANALYTE | 1 | 2 | 3 | 4 | 5 | 6 | 7 | 8 | 9 |
| RESULT | 68 | 9 | 9.3 | 108 | 2.0 | 6.0 | 222 | 3.3 | 160 |

In step 4 of the method of the present invention a patient analyte level set including an analyte level for each analyte value in the patient test result set is generated using the information maintained in the first database. In a preferred embodiment of the present invention, the analyte level set is generated by first generating a percent status set. The percent status set includes a value for each analyte value in the patient test result set. The percent status value is indicative of a relationship between the individual's analyte values and the test group's analyte values. The percent status set is generated by calculating a percent status value for each analyte value in the patient test result set. The percent status is calculated using one of the following equations:

if the individual's analyte value is greater than the analyte target value than, % Status=50*(patient test result analyte value−analyte target value)/(analyte high value−analyte target value)

if the individual's analyte value is less than the analyte target value than,

% Status=50*(patient test result analyte value−analyte target value)/(analyte target value−analyte low value)

Table 5 presents the results of calculating the percent status for each of the analyte values of the patient test result set presented in Table 4. The percent status results are also presented in Table 3 for easy comparison with the other parameters.

TABLE 5

| ANALYTE | 1 | 2 | 3 | 4 | 5 | 6 | 7 | 8 | 9 |
|---|---|---|---|---|---|---|---|---|---|
| % STATUS | −17 | −21 | −14 | 42 | 43 | 15 | 37 | −10 | −30 |
| PRESENCE LEVEL | N | N | N | H | L | N | H | N | L |

By determining the percent status as a function of the analyte target value and changing the denominator of the above referenced equations based upon the relationship of the individual's analyte value and the target value, the percent status provides a very accurate and true picture of the individual's analyte level relative to the healthiest value for the analyte, as indicated by the target value. This is in contrast to prior attempts to compare the individual's analyte values to human test group analyte values. In the past, the comparison between the individual's analyte values and the human test group analyte values utilized the mathematical average between the low value and the high value, also known as the mean. The use of the mean value instead of the target value presents the following potential drawback. Only in the rare instance that the results of the human test group present a symmetrical bell curve will the mean value and the target value will be the same. However, if the human test group does not present a symmetrical bell curve, than the mean value will not equal the mode value. In this instance, the mean value will merely represent a mathematical average between the low value and the high value. This value will not be representative of the healthiest human value for the particular analyte. As such, any analysis based upon the mean value will suggest to the practitioner to drive the individual's analyte values to a mathematical average and not to the optimum human values, as indicated by the human test group results and the resultant target value.

Once the percent status set is generated, the percent status result for each analyte is compared to a preselected high status value and a preselected low status value. This comparison forms the basis for determining the individual's analyte level for each particular analyte relative to the test group. In a preferred embodiment of the present invention, the preselected low status value is −25 and the preselected high status value is 25. For all of the percent status set elements having a value less than or equal to −25, the corresponding elements of the patient analyte level set are labeled LOW. For all of the percent status set elements having a value greater than −25 but less than 25, the corresponding elements of the patient analyte level set are labeled NORMAL. For all of the percent status set elements having a value greater than or equal to 25, the corresponding elements of the patient analyte level set are labeled HIGH.

Table 5 presents the results of step 4, wherein an "L" represents a LOW level presence, an "N" represents a NORMAL level presence and a "H" represents a HIGH level presence of the various analytes. For further understanding, the patient analyte level presence of step 4 (L, N or H) are also presented in Table 3.

By generating the patient analyte level set based upon a percent status value that is a function of the target value for the particular analyte, a practitioner will be better able to adjust the individual's analyte levels towards a normal, optimal human condition. In other words, the use of the target value provides an analyte offset or percent status relative to the analyte value of the most common human analyte level. By using the offset relative to the target value in prescribing a course of action, the practitioner is better able to drive the individual's analyte values to the target values, these values being considered the optimum values.

In step 5 of the method of the present invention, the patient analyte level set is compared to each of the vitamin/nutrient records of the second database. This comparison provides the basis for determining any correlation between the individual's analyte values and vitamins/nutrients maintained in the second database.

In step 6 of the method of the present invention, a determination is made, based upon the comparison of step 5, regarding any correlation between the patient analyte level set and each of the vitamin/nutrient records of the second database. The correlation between the patient analyte level set and the vitamin/nutrient records will indicate whether an individual will benefit from a particular vitamin/nutrient. The comparison indicates a group of vitamins/nutrients that has supportive effects for the individual in light of the analyte levels by counting how many "pattern matches" exist between the analyte levels (L, N or H) of the patient analyte level set and the analyte levels for the various analytes associated with the particular vitamin/nutrient of the second database.

TABLE 6

Vitamin/Nutrient Indicator

| VITAMIN/NUTRIENT | # ANALYTES | # MATCHES | % MATCH |
|---|---|---|---|
| 1 | 5 | 0 | 0% |
| 2 | 6 | 4 | 67% |
| 3 | 5 | 2 | 40% |
| . | . | . | . |
| . | . | . | . |
| . | . | . | . |

Table 6 presents an example of the results of a comparison between the presence level of analytes associated with a particular vitamin/nutrient and the presence level of the corresponding analytes of the individual's analyte level set. The analyte presence levels (L, N or H) of the various analytes of the patient analyte level set are compared with the analyte presence levels of the analytes associated with the various vitamin/nutrient, for example vitamin/nutrient1, 2, 3, . . . maintained in the second database and presented in Table 3. This comparison enables the system to determine the degree to which any of the vitamin/nutrient are indicated. By determining a percent match between the individual's analyte presence levels and the analyte presence levels for analytes associated with a particular vitamin/nutrient, as presented in the last column of Table 6, the method of the present invention can determine the likelihood that a vitamin/nutrient will have a supportive effect. For example, as presented in Table 6, vitamin/nutrient 2 is very likely called for because 4 of 6 of the analyte levels are matched, whereas vitamins/nutrients 1 and 3 are not likely called for because fewer of the analyte levels for these vitamins/nutrients are matched.

In another preferred embodiment of the present invention, generating the patient analyte level set is accomplished in an alternative manner. In particular, where the manner described above for generating the patient analyte level set generated the percent status set and determined the analyte presence levels based upon the percent status set, the present manner generates a normal limit set. The normal limit set comprises analyte values that demarcate the boundaries for normal levels of the particular analyte. The normal limit set includes a high normal limit and a low normal limit.

Figure 5:
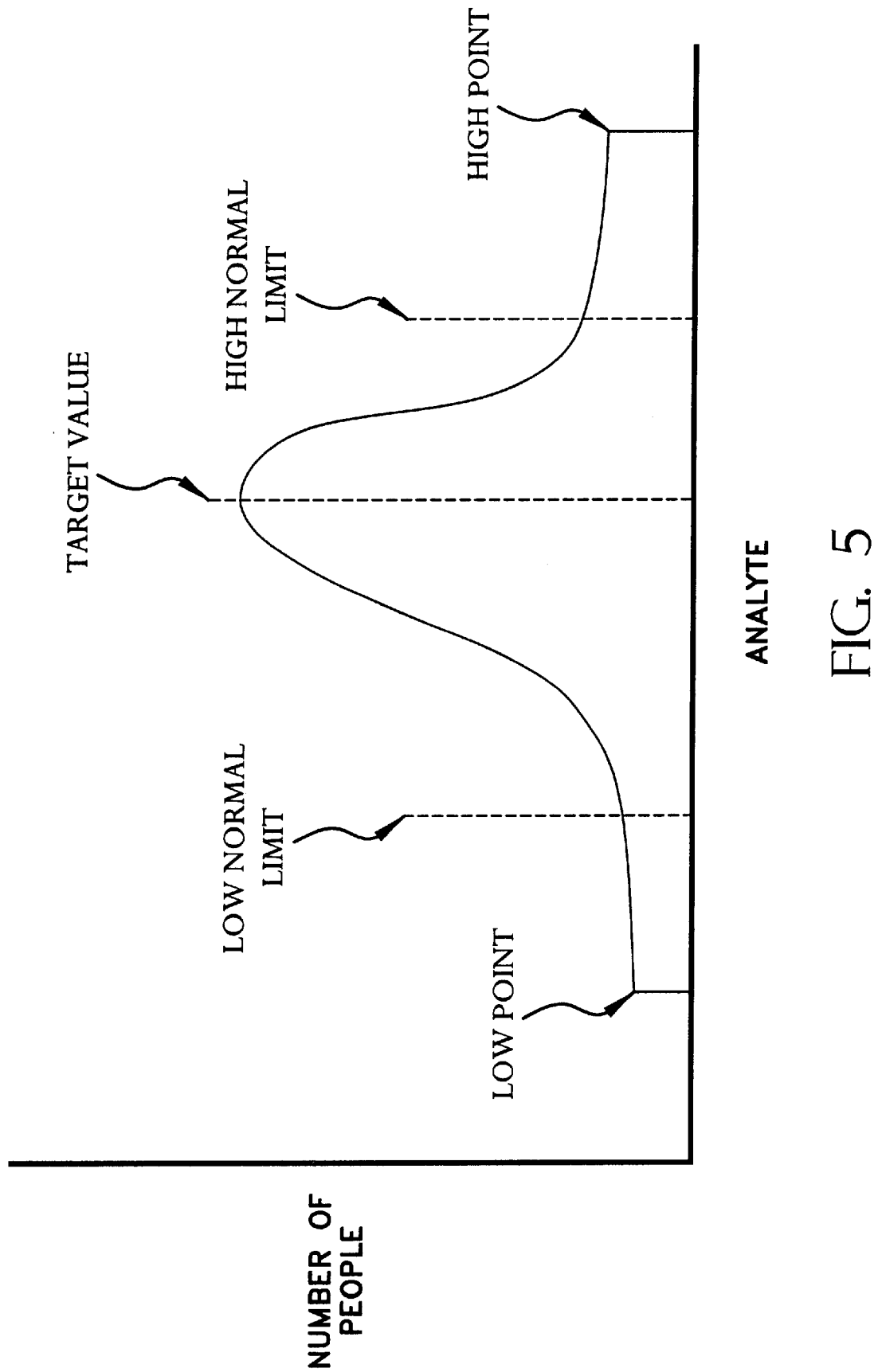
FIG. 5 is a graph illustrating another manner in which High, Low and Normal levels of an analyte are determined in conjunction with the present invention.

As illustrated in FIG. 5, a curve indicative of test results obtained from the human test group, as described above is a frequency distribution curve. The curve includes a lower limit, labeled "Low Point" and an upper limit, labeled "High Point." The Low Point and the High Point are determined as two standard deviations of the results of the human test group. In generating the analyte level set, the method of the present invention implementing the alternative manner of generating the patient analyte level set requires a demarcation for LOW levels, NORMAL levels, and HIGH levels. In this embodiment, the method generates a normal limit value set for each of the plurality of analytes maintained in the first database using the data information maintained in each record of the first database. The normal limit value set includes a high normal limit value (HNL) and a low normal limit (LNL) value.

The high normal limit value for each analyte is determined using the equation:

HNL=analyte target value+[normal percent range*(analyte high value−analyte target value)]

The low normal limit value for each analyte is determined using the equation:

LNL=analyte target value−[normal percent range*(analyte target value−analyte low value)]

The normal percent range is a constant between 0 and 1. The normal percent range is preferably between 0.25 and 0.75. The normal percent range is more preferably 0.50. For all of the analyte values of the patient analyte test result set that are less than or equal to LNL, the corresponding elements of the patient analyte level set are labeled LOW. For all of the analyte values of the patient analyte test result set that are greater than the LNL but less than the HNL, the corresponding elements of the patient analyte level set are labeled NORMAL. For all of the analyte values of the patient analyte test result set that are greater than or equal to the HNL, the corresponding elements of the patient analyte level set are labeled HIGH.

As discussed above, by generating the HNL and the LNL as a function of the analyte target value and changing the denominator for each, the determination of the presence levels provides a more accurate indicator of the individual's analyte values relative to the healthiest analyte value, as shown by the target value. This in turn provides the practitioner with a better basis for developing a course of treatment.

Therefore, the basic method presented in FIG. 2 enables a medical practitioner to input an individual's analyte values into a computerized system and have the system produce a listing of vitamins/nutrients that will have a supportive effect on that individual's analyte levels based upon the variation between the individual's analyte values and the analyte values of a human test group.

A further feature of the present invention is the generation of a report indicating the known effects of various drugs on analyte levels. As illustrated in step of FIG. 6 and presented as an example in Table 7, a third database is created and stored on the storage medium. The third database includes drug records that correlate the effects of known drugs upon the levels of each of the various analytes. Thus, as presented in Table 7, for each analyte 1, 2, 3 . . . known drugs are cataloged that can cause or increase an analyte value that has already been determined to be a HIGH analyte presence level (H) and that can cause or decrease an analyte value that has already been determined to be a LOW analyte presence level (L). The effects of the various drugs on the various analyte levels are well known in medical research and new drugs, and the corresponding effects thereof on various analytes are developed in medical research on a daily basis.

TABLE 1

| | DRUG (a, b, c. . .) CAUSE OR AGGRAVATE | |
|---|---|---|
| ANALYTE | HIGH (H) | LOW (L) |
| 1 | a, b, d, f, h | l, m, p |
| 2 | a, c, e, j, l | b, d, o, p |
| 3 | b, c, f, g | d, j, k, l, m |
| 4 | a, d, g, h | b, f, k |
| 5 | a, c, f, h, k, l | b, d, e, o, p |
| 6 | e, h, k, m | a, d, l, r, t |
| . | . | . |
| . | . | . |
| . | . | . |

Figure 6:
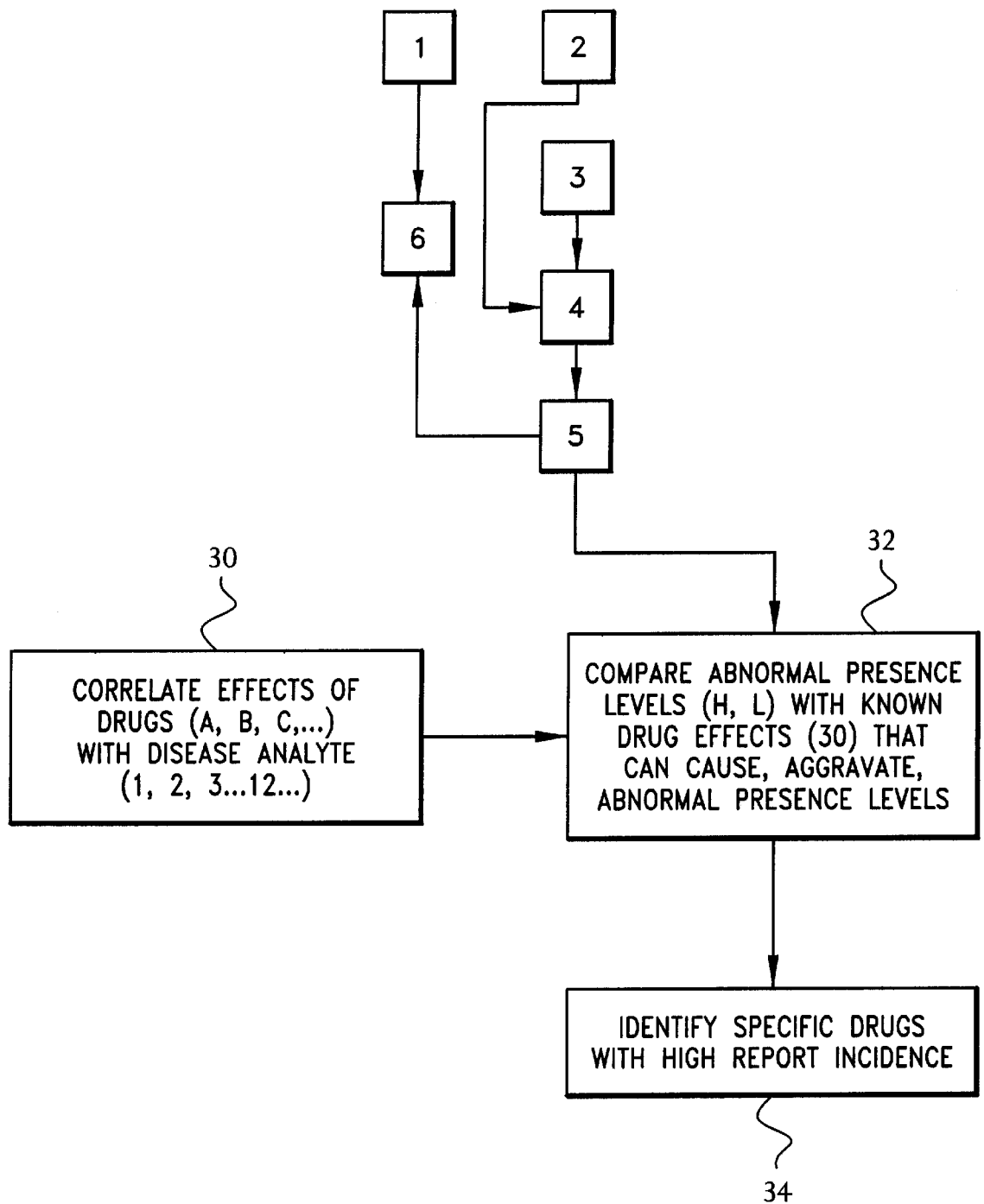
FIG. 6 is a block diagram showing the incorporation of known drug effect data with analyte status levels o the present invention.

As illustrated in FIG. 6, the next step 32 in this analysis is to compare the abnormal presence levels, both HIGH (H) and LOW (L), determined in step 4 of the basic method of the present invention, with the drug effects data presented in Table 7. By way of example, Table 5 shows that a specific individual's test results indicated that analytes 1 and 2 showed a NORMAL presence level, analyte 3 had a LOW presence level, analyte 4 had a HIGH presence level, and analytes 5 and 6 had LOW presence levels.

Table 8 presents the abnormal analytes 3, 4, 5 and 6, their HIGH or LOW presence level, and identifies the specific drugs from Table 7 that cause HIGH or LOW presence level of the analyte, as described above.

TABLE 8

| ANALYTE | ABNORMAL PRESENCE LEVEL | DRUG CAUSE OR AGGRAVATE |
|---|---|---|
| 3 | L | d, j, k, l, m |
| 4 | H | a, d, g, h |
| 5 | L | b, d, e, o, p |
| 6 | L | a, d, l, r, t |
| . | . | . |
| . | . | . |
| . | . | . |

HIGH INCIDENCE DRUG = d (CONTRAINDICATED)

After comparing the analyte presence levels and the drugs related to the particular analyte, as presented in Tables 7 and 8 the incidence of the various drugs presented in Table 15 is determined, as set indicated by step 34 of FIG. 6. Specifically, it can be seen in Table 8 that drug "d" is identified as a drug that can cause or aggravate each of the abnormal presence levels of each of the analytes presented in Table 8. The analytical result of this analysis is the conclusion that drug "d" is contraindicated for this individual.

To further enhance the understanding of the present invention, Table 9 presents known drug effect medical research data for a few specific analyte conditions. Specifically, for the analyte chloride level in blood testing, where the chloride level is high (percent status is greater than 25), some known drugs that can cause or aggravate this condition are listed; aspirin is one of these drugs. For the total iron level analyte, which is low (percent status is less than −25), some known drugs that can cause or aggravate this reduced level are provided. For the basophils analyte level, which is low (percent status is less than −25), a drug that can cause or aggravate this low level is procainamide. For the white blood count (WBC) level analyte having a low level (percent status is less than −25), drugs that can cause or aggravate this reduced level are listed, and it is specifically noted that aspirin is one of the drugs. For the glucose level analyte having a low level (percent status is less than −25), drugs which cause or aggravate the low level are identified, and it is specifically noted that aspirin is one such drug. The last analyte presented in Table 9 (it being understood that as many analytes as are identified in test results as having an high or low levels would be included in Table 9) is total protein having a low level (percent status is less than −25), and some of the various drugs that can cause or aggravate the reduced level are identified, specifically identifying aspirin as one of the drugs.

TABLE 9

| ANALYTE | ABNORMAL PRESENCE LEVEL | DRUG CAUSE OR AGGRAVATE CONDITION |
|---|---|---|
| Chloride | L | Acetazolamide, Aspirin, Lithium, Boric Acid... |
| Total iron | L | ACTH, Oxalate, Fluorides... |
| Basophils | L | Procainamide... |

TABLE 9-continued

| ANALYTE | ABNORMAL PRESENCE LEVEL | DRUG CAUSE OR AGGRAVATE CONDITION |
|---|---|---|
| WBC | L | Aspirin, Busulfan, Mepazine... |
| Glucose | L | Aspirin, Ethanol, Insulin |
| Total Protein | L | Aspirin, Arginine, Rifampin... |

An analysis of the data presented in Table 9 shows that the drug aspirin is identified as a drug that can cause or aggravate four of the six abnormal presence levels of the analytes set forth therein; thus aspirin is a contraindicated drug for the individual whose test results are provided in Table 9.

It is therefore to be generally understood that the present invention includes a method as shown in FIG. 6 to identify specific drugs that are contraindicated for an individual based upon the high or low levels of specific analytes in the individual's blood/fluid test analysis results. This output data of contraindicated drugs is obtained utilizing a database 30 that correlates high and low analyte levels with known drug effects from known medical research, and the specific analytes identified in step 5 test results as having high or low levels pursuant to the analytical methods of the present invention.

Figure 7:
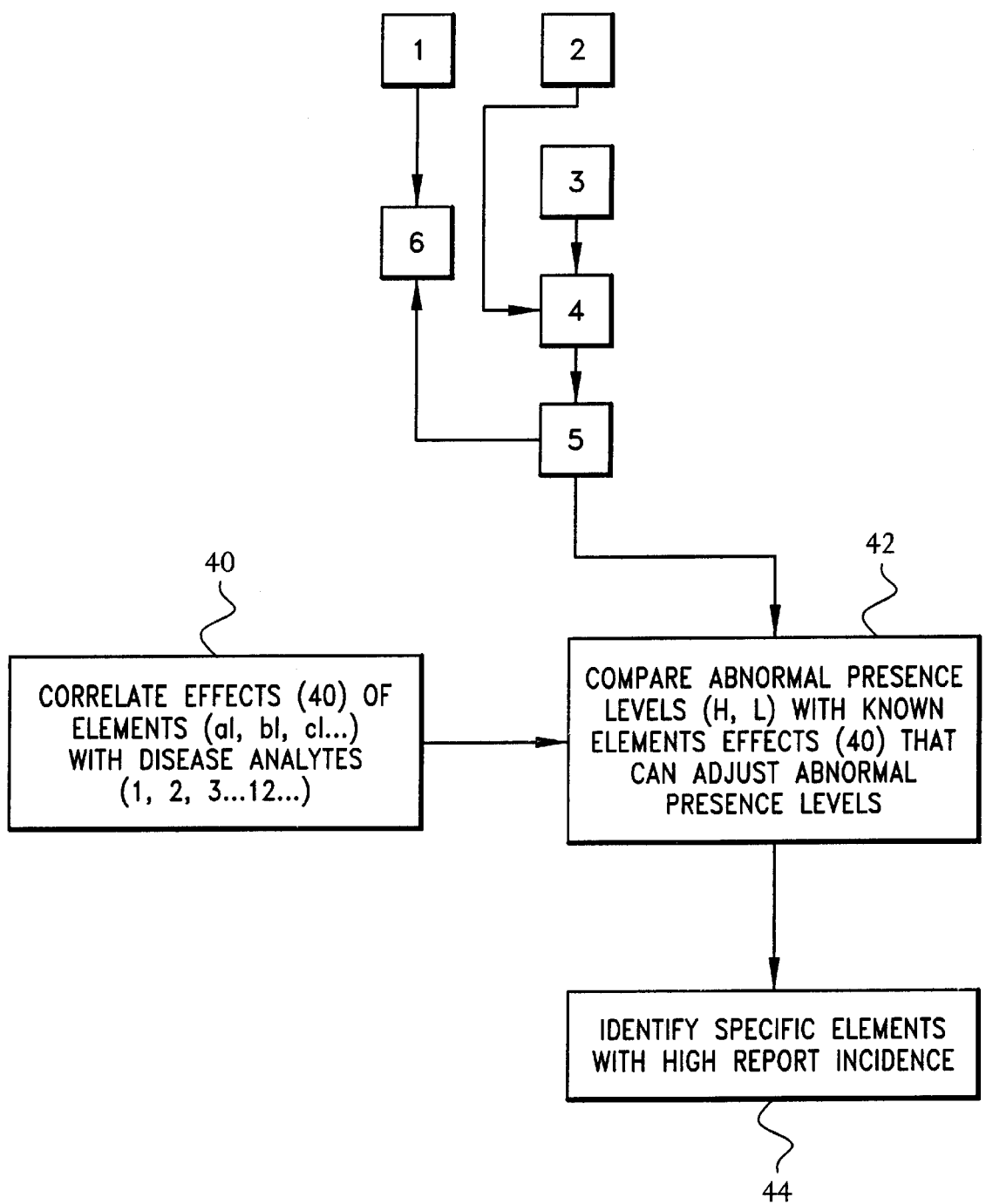
FIG. 7 is a block diagram showing the utilization of known effects of nutritional-biochemical elements with analyte levels.

Another feature of the present invention is the incorporation of the known positive effects of various pharmacological agents upon test results for various analyte levels. As illustrated in FIG. 7, and the example presented in Table 10, a pharmacological agents database 40 is created and stored in the storage medium. The agents database includes agent records that correlate the effects of known pharmacological agents (a1, b1, c1, . . .) upon the levels for each of the various analytes. Table 10 is similar to Table 7 with the significant difference that the effect of the pharmacological agents is to improve the abnormal presence level of various analytes.

TABLE 10

| | PHARMACOLOGICAL AGENT (a1, b1, c1...) EFFECT | |
|---|---|---|
| ANALYTE | INCREASE (I) | DECREASE (D) |
| 1 | bl, dl, fl, hl | cl, dl, rl |
| 2 | al, gl, ll | cl, ll, sl, tl |
| 3 | dl, gl, hl, kl | bl, cl, ml |
| 4 | al, kl, ml | cl, dl, ll |
| 5 | cl, kl, rl, sl | al, fl, gl, ml, pl |
| 6 | al, cl, nl, tl, vl | dl, hl, kl, ml, sl |
| . | . | . |
| . | . | . |
| . | . | . |

Thus, as presented in Table 10, for each analyte 1, 2, 3 . . . 12 . . . known agents are cataloged that can normalize the level of a particular analyte; that is, to reduce an high level or to raise a low level. The effects or the various pharmacological agents on the various analyte levels are well known in medical research. New agents, and the corresponding effects thereof on various analytes are developed in medical research on a daily basis.

As illustrated in FIG. 7, the next step 42 in this analysis is to compare the abnormal presence levels, both high (H) and low (L), determined in step 4 of the basic method of the present invention with the pharmacological agent data of Table 10. By way of example, it is presented above in Table 5 that a specific individual's test results showed that analytes 1 and 2 showed a normal presence level, analyte 3 had a low presence level, analyte 4 had an high presence level, analytes 5 and 6 had low presence levels. Table 10 presents the abnormal analytes 3, 4, 5 and 6 with their high or low presence level, and identifies the specific pharmacological agents from Table 10 that can have a positive effect on the abnormal presence level indicated.

TABLE 11

| ANALYTE | ABNORMAL PRESENCE LEVEL | PHARMACOLOGY AGENT EFFECT. |
|---|---|---|
| 3 | L | bl, cl, ml |
| 4 | H | al, kl, ml |
| 5 | L | al, fl, gl, ml, pl |
| 6 | L | dl, hl, kl, ml, sl |
| . | . | . |
| . | . | . |
| . | . | . |

HIGH INCIDENCE AGENT = ml (INDICATED)

Thereafter, in step 44 of FIG. 7, the incidence of the various pharmacological agents presented in Table 11 is determined. Specifically, it is seen in Table 11 that pharmacological agent "ml" is identified as an agent that can have a positive effect on each of the abnormal presence levels of each of the analytes. The analytical result of this analysis is the conclusion that pharmacological agent "ml" is positively indicated for this individual.

Another feature of the present invention enables the merging of two or more test results (each test including a distinct panel of analytes) to provide a single (combined) nutritional assessment for the individual for which the tests pertain, wherein the assessment provides a group of vitamins/nutrients having supportive effects on the individual's analyte levels based upon the two or more test results. The assessment is arrived at by the same methods described above. The same may be provided for a drug report.

Another feature of the present invention enables the group of vitamins/nutrients having a supportive effect on the analyte levels to be determined based upon multiple analyte levels. Specifically, the present invention includes determining the group of vitamins/nutrients by correlating at least two of the plurality of analytes based upon similar supportive effects of a particular vitamin/nutrient on the levels of the at least two analytes and selecting the group of vitamins/nutrients based upon the comparison of the patient analyte level set to the plurality of vitamin/nutrient records and the correlation of the at least two plurality of analytes.

For example, with reference to table 12, magnesium sulfate may be selected as part of a group of vitamins/nutrients based upon the following. The levels of a plurality of analytes (Alkaline Phosphatase, GGT and Calcium) of an individual are compared to a vitamin/nutrient record. It is known that if Alkaline Phosphatase is Low (below −15% of the target value in this case) or GGT is Low or Calcium is Low or High (above +15% of the target value in this case) then Magnesium is recommended. If Chloride is High than Sulfur is recommended while if CO2 is lower then +15 % than Sulfur is contraindicated. Therefore, if all of these conditions are met, than Magnesium Sulfate (Epsom Salts) is recommended. As the percent status of Chloride increases, the importance of taking Magnesium Sulfate increases. By correlating several of the analytes, any report can accurately and easily indicate the inclusion, exclusion and modification of a particular vitamin/nutrient. Furthermore, any report which indicates the group of vitamins/nutrients which are suggested, can also indicate the importance of a particular vitamin/nutrient by use of a star system.

TABLE 12

| Magnesium Sulfate | | 1 Star | 2 Star | 3 Star | 4 Star |
|---|---|---|---|---|---|
| | Alkaline Phosphatase | <−15 | <−15 | <−15 | <−15 |
| or | | | | | |
| | GGT | <−15 | <−15 | <−15 | <−15 |
| or | | | | | |
| | Calcium | <−15 or >+15 | <−15 or >+15 | <−15 or >+15 | <−15 or >+15 |
| and | | | | | |
| | Chloride | >+15 | >+25 | >+35 | >+45 |
| and | | | | | |
| | CO2 | >−5 | >−5 | >−5 | |

While the present invention has been described with reference to certain preferred embodiments, it is to be understood that the present invention is not to be limited to such specific embodiments. Rather, it is the inventors intention that the invention be understood and construed in its broadest meaning as reflected by the following claims.

Thus, these claims are to be understood as incorporating and not only the preferred embodiment described herein but all those other and further alterations and modifications as would be apparent to those of ordinary skill in the art.

What is claimed is:

1. A method for identifying supportive vitamins/nutrients utilizing a central processing unit and a storage medium coupled to the central processing unit, comprising the steps of:

storing a first database for maintaining analyte data information for a plurality of analytes in the storage medium, the first database including an analyte record for each one of the plurality of analytes, each analyte record including an analyte low value, an analyte high value and an analyte target value selected from the group consisting of mode value and weighted average value indicative of a statistical analysis of analyte values obtained from testing a human test group, and wherein the weights of the weighted average do not all equal one;

storing a second database for maintaining vitamin/nutrient information for a plurality of vitamins/nutrients in the storage medium, the second database including a vitamin/nutrient record for each one of the plurality of vitamins/nutrients, each vitamin/nutrient record including a set of analytes associated with the particular vitamin/nutrient and an effect the particular vitamin/nutrient has on the associated analytes;

inputting a patient analyte test result set into the central processing unit, the patient analyte test result set including an analyte value for at least one of the plurality of analytes;

generating a patient analyte level set from the patient analyte test result set and the analyte data information of the first database, the patient analyte level set including a patient analyte level for each analyte in the analyte test result set;

comparing the patient analyte level set to each of the plurality of vitamin/nutrient records; and determining a group of vitamins/nutrients that has supportive effects on the patient analyte levels.

2. A method for identifying supportive vitamins and nutrients as set forth in claim 1, wherein the step of generating the patient analyte level set comprises the step of generating a patient percent status set, the patient percent status set comprising a value for each of the plurality of analytes in the patient analyte test result set.

3. A method for identifying supportive vitamins and nutrients as set forth in claim 2, wherein the step of generating the patient percent status set comprises calculating a percent status value for each element of the patient percent status set using the following:

if the patient analyte test result value is greater than the analyte target value then percent status=50*(patient analyte test result value−analyte target value)/(analyte high value−analyte target value)

and, if the patient analyte test result value is less than the analyte target value then percent status=50*(patient analyte test result value−analyte target value)/(analyte target value−analyte low value).

4. A method for identifying supportive vitamins and nutrients as set forth in claim 3, wherein the step of generating the patient analyte level set further comprises the step of comparing the patient percent status set to a preselected high status value and a preselected low status value.

5. A method for identifying supportive vitamins and nutrients as set forth in claim 4, wherein the preselected high status value is 25 and the preselected low status value is −25.

6. A method for identifying supportive vitamins and nutrients as set forth in claim 5, wherein the step of generating the patient analyte level set further comprises the step of labeling the analyte level for each element of the patient analyte level set LOW if corresponding elements of the patient percent status set are less than or equal to −25, labeling the analyte level for each element of the patient analyte level set NORMAL if corresponding elements of the patient percent status set are greater than −25 and less than 25, and labeling the analyte level for each element of the patient analyte level set HIGH if corresponding elements of the patient percent status set are greater than or equal to 25.

7. A method for identifying supportive vitamins and nutrients as set forth in claim 1, wherein the step of generating the patient analyte level set comprises the step of generating a normal limit value set for each of the plurality of analytes.

8. A method for identifying supportive vitamins and nutrients as set forth in claim 7, wherein the normal limit value set includes a high normal limit value and a low normal limit value.

9. A method for identifying supportive vitamins and nutrients as set forth in claim 8, wherein the high normal limit value is given by the equation high normal limit value=analyte target value+(normal percent range)*(analyte high value−analyte target value)

and the low normal limit value is given by the equation, low normal limit value=analyte target value−(normal percent range)*(analyte target value−analyte low value), wherein the normal percent range being a preselected value between 0 and 1.

10. A method for identifying supportive vitamins and nutrients as set forth in claim 9, wherein the step of generating the patient analyte level set further comprises the step of labeling the elements of the patient analyte level set LOW if the corresponding elements of the patient analyte test result set are less than the low normal limit value, labeling the elements of the patient analyte level set NORMAL if the corresponding elements of the patient analyte test result set are greater than the low normal limit value and less than the high normal limit value, and labeling the elements of the patient analyte level set HIGH if the corresponding elements of the patient analyte test result set are greater than the high normal limit value.

11. A method for identifying supportive vitamins and nutrients as set forth in claim 1, further comprising the step of gathering the vitamin/nutrient information for a plurality of vitamins/nutrients and generating the second database.

12. A method for identifying supportive vitamins and nutrients as set forth in claim 1, wherein the plurality of analytes comprises red cell membrane fatty acids.

13. A method for identifying supportive vitamins and nutrients as set forth in claim 1, wherein the plurality of analytes comprises blood analytes.

14. A computer program embodied on a computer-readable medium for analyzing analyte levels of an individual, comprising:

an analysis source code including instructions to (a) receive a patient analyte test result set, the patient the patient analyte test result set including an analyte value for a plurality of analytes; (b) generate a patient analyte level set from the patient analyte test result set and a first database, the first database maintaining analyte data information for a plurality of analytes and including an analyte record for each one of the plurality of analytes, each analyte record including an analyte low value, an analyte high value and an analyte target value selected from the group consisting of mode value and weighted average value indicative of a statistical analysis of analyte values obtained from testing a human test group, and wherein the weights of the weighted average do not all equal one, the patient analyte level set including a patient analyte level for each analyte in the analyte test result set; (c) compare the patient analyte level set to a second database, the second database maintaining vitamin/nutrient information for a plurality of vitamins/nutrients and including a vitamin/nutrient record for each one of the plurality of vitamins/nutrients, each vitamin/nutrient record including a set of analytes associated with the particular vitamin/nutrient and an effect the particular vitamin/nutrient has on the associated analytes; and (d) determine a group of vitamins/nutrients that has supportive effects on the patient analyte levels.

15. A computer program embodied on a computer-readable medium as set forth in claim 14, wherein the instructions to generate the patient analyte level set comprise instructions to generate a patient percent status set, the patient percent status set including a value for each of the plurality of analytes in the patient analyte test result set.

16. A computer program embodied on a computer-readable medium as set forth in claim 15, wherein the instructions to generate the patient percent status set comprise instructions to calculate a percent status value for each element of the patient percent status set using the following:

if the patient analyte test result value is greater than the analyte target value then percent status=50*(patient analyte test result value−analyte target value)/(analyte high value−analyte target value)

and, if the patient analyte test result value is less than the analyte mode value then percent status=50*(patient analyte test result value−analyte target value)/(analyte target value−analyte low value).

17. A computer program embodied on a computer-readable medium as set forth in claim 16, wherein the instructions to generate the patient analyte level set further comprise instructions to compare the patient percent status set to a preselected high status value and a preselected low status value.

18. A computer program embodied on a computer-readable medium as set forth in claim 17, wherein the preselected high status value is 25 and the preselected low status value is −25.

19. A computer program embodied on a computer-readable medium as set forth in claim 18, wherein the instructions to generate the patient analyte level set further comprise instructions to label the analyte level for each element of the patient analyte level set LOW if corresponding elements of the patient percent status set are less than or equal to −25, label the analyte level for each element of the patient analyte level set NORMAL if corresponding elements of the patient percent status set are greater than −25 and less than 25, and label the analyte level for each element of the patient analyte level set HIGH if corresponding elements of the patient percent status set are greater than or equal to 25.

20. A computer program embodied on a computer-readable medium as set forth in claim 14, wherein the instructions to generate the patient analyte level set comprise instructions to generate a normal limit value set for each of the plurality of analytes.

21. A computer program embodied on a computer-readable medium as set forth in claim 20, wherein the normal limit value set includes a high normal limit value and a low normal limit value.

22. A computer program embodied on a computer-readable medium as set forth in claim 21, wherein the high normal limit value is given by the equation high normal limit value=analyte target value+(normal percent range)*(analyte high value−analyte target value)

and the low normal limit value is given by the equation, low normal limit value=analyte target value−(normal percent range)*(analyte target value−analyte low value), wherein the normal percent range being a preselected value between 0 and 1.

23. A computer program embodied on a computer-readable medium as set forth in claim 22, wherein the instructions to generate the patient analyte level set further comprise instructions to label the elements of the patient analyte level set LOW if the corresponding elements of the patient analyte test result set are less than the low normal limit value, label the elements of the patient analyte level set NORMAL if the corresponding elements of the patient analyte test result set are greater than the low normal limit value and less than the high normal limit value, and label the elements of the patient analyte level set HIGH if the corresponding elements of the patient analyte test result set are greater than the high normal limit value.

24. A medical diagnostic method utilizing a central processing unit and a storage medium coupled to the central processing unit, comprising the steps of:

storing a first database for maintaining analyte data information for a plurality of analytes in the storage medium, the first database including an analyte record for each one of the plurality of analytes, each analyte record including an analyte low value, an analyte high value and an analyte target value selected from the group consisting of mode and weighted average value indicative of a statistical analysis of analyte values obtained form testing a human test group, and wherein the weights of the weighted average do not all equal one;

storing a second database for maintaining drug data information for a plurality of drugs in the storage medium, the second database including a drug record for each one of the plurality of drugs, each drug record including a set of analytes associated with the particular drug, each analyte of the analyte set having an analyte level indicative of the particular drug;

inputting a patient analyte test result set into the central processing unit, the patient analyte test result set including an analyte value for at least one of the plurality of analytes;

generating a patient analyte level set from the patient analyte test result set and the analyte data information of the first database;

comparing the patient analyte level set to each of the plurality of drug records; and determining a correlation between the patient analyte level set and each of the drug records.

25. A medical diagnostic method as set forth in claim 24, wherein the step of generating the patient analyte level set comprises the step of generating a patient percent status set, the patient percent status set comprising a value for each of the plurality of analytes in the patient analyte test result set.

26. A medical diagnostic method as set forth in claim 25, wherein the step of generating the patient percent status set comprises calculating a percent status value for each element of the patient percent status set using the following:

if the patient analyte test result value is greater than the analyte target value then percent status=50*(patient analyte test result value−analyte target value)/(analyte high value−analyte target value)

and, if the patient analyte test result value is less than the analyte target value then percent status=50*(patient analyte test result value−analyte target value)/(analyte target value−analyte low value).

27. A medical diagnostic method as set forth in claim 26, wherein the step of determining the patient analyte level set further comprises the step of comparing the patient percent status set to a preselected high status value and a preselected low status value.

28. A medical diagnostic method as set forth in claim 27, wherein the preselected high value is 25 and the preselected low value is −25.

29. A medical diagnostic method as set forth in claim 28, wherein the step of generating the patient analyte level set further comprises the step of labeling the analyte level for each element of the patient analyte level set LOW if corresponding elements of the patient percent status set are less than or equal to −25, labeling the analyte level for each element of the patient analyte level set NORMAL if corresponding elements of the patient percent status set are greater than −25 and less than 25, and labeling the analyte level for each element of the patient analyte level set HIGH if corresponding elements of the patient percent status set are greater than or equal to 25.

30. A medical diagnostic method as set forth in claim 24, wherein the step of generating the patient analyte level set comprises the step of generating a normal limit value set for each of the plurality of analytes.

31. A medical diagnostic method as set forth in claim 30, wherein the normal limit value set includes a high normal limit value and a low normal limit value.

32. A medical diagnostic method as set forth in claim 31, wherein the high normal limit value is given by the equation, high normal limit value=analyte target value+(normal percent range)*(analyte high value−analyte target value)

and the low normal limit value is given by the equation, low normal limit value=analyte target value−(normal percent range)*(analyte target value−analyte low value), the normal percent range being a preselected value between 0 and 1.

33. A medical diagnostic method as set forth in claim 32, wherein the step of determining the patient analyte level set further comprises the step of labeling the elements of the patient analyte level set LOW if the corresponding elements of the patient analyte test result set are less than the low normal limit value, labeling the elements of the patient analyte level set NORMAL if the corresponding elements of the patient analyte test result set are greater than the low normal limit value and less than the high normal limit value, and labeling the elements of the patient analyte level set HIGH if the corresponding elements of the patient analyte test result set are greater than the high normal limit value.

34. A medical diagnostic method as set forth in claim 24, further comprising the step of gathering the analyte data information and generating the first database.

35. A medical diagnostic method as set forth in claim 24, wherein the plurality of analytes comprises red cell membrane fatty acids.

36. A medical diagnostic method as set forth in claim 24, wherein the plurality of analytes comprises blood analytes.

37. A method for identifying supportive vitamins/nutrients utilizing a central processing unit and a storage medium coupled to the central processing unit, comprising the steps of:

storing a first database for maintaining analyte data information for a plurality of a first type analytes and a plurality of a second type of analytes in the storage medium, the first database including an analyte record for each one of the analytes, each analyte record including an analyte low value, an analyte high value and an analyte target value selected from the group consisting of mode value and weighted average value indicative of a statistical analysis of analyte values obtained from testing a human test group, and wherein the weights of the weighted average do not all equal one;

storing a second database for maintaining vitamin/nutrient information for a plurality of vitamins/nutrients in the storage medium, the second database including a vitamin/nutrient record for each one of the plurality of vitamins/nutrients, each vitamin/nutrient record including a set of analytes associated with the particular vitamin/nutrient and an effect the particular vitamin/nutrient has on the associated analytes;

inputting a patient analyte test result set into the central processing unit, the patient analyte test result set including an analyte value for each of the first type of analytes and the second type of analytes;

generating a patient analyte level set from the patient analyte test result set and the analyte data information of the first database, the patient analyte level set including a patient analyte level for each analyte in the analyte test result set;

comparing the patient analyte level set to each of the plurality of vitamin/nutrient records; and determining a group of vitamins/nutrients that has supportive effects on the patient analyte levels.

38. A medical diagnostic method utilizing a central processing unit and a storage medium coupled to the central processing unit, comprising the steps of:

storing a first database for maintaining analyte data information for a plurality of a first type of analytes and a plurality of a second type of analytes in the storage medium, the first database including an analyte record for each one of the plurality of analytes, each analyte record including an analyte low value, an analyte high value and an analyte target value selected from the group consisting of mode value and weighted average value indicative of a statistical analysis of analyte values obtained from testing a human test group, and wherein the weights of the weighted average do not all equal one;

storing a second database for maintaining drug data information for a plurality of drugs in the storage medium, the second database including a drug record for each one of the plurality of drugs, each drug record including a set of analytes associated with the particular drug, each analyte of the analyte set having an analyte level indicative of the particular drug;

inputting a patient analyte test result set into the central processing unit, the patient analyte test result set including an analyte value for each of the first type of analytes and the second type of analytes;

generating a patient analyte level set from the patient analyte test result set and the analyte data information of the first database;

comparing the patient analyte level set to each of the plurality of drug records; and determining a correlation between the patient analyte level set and each of the drug records.

39. A method for identifying supportive vitamins/nutrients as recited in claim 1, wherein the step of determining a group of vitamins/nutrients comprises the steps of correlating at least two of the plurality of analytes based upon similar supportive effects of a particular vitamin/nutrient on the levels of the at least two analytes and selecting the group of vitamins/nutrients based upon the comparison of the patient analyte level set to the plurality of vitamin/nutrient records and the correlation of the at least two plurality of analytes.

40. A computer program as recited in claim 14, wherein the instructions to determine a group of vitamins/nutrients comprise instructions to correlate at least two of the plurality of analytes based upon similar supportive effects of a particular vitamin/nutrient on the levels of the at least two analytes and select the group of vitamins/nutrients based upon the comparison of the patient analyte level set to the plurality of vitamin/nutrient records and the correlation of the at least two plurality of analytes.

41. A method for identifying supportive vitamins/nutrients as recited in claim 37, wherein the step of determining a group of vitamins/nutrients comprises the steps of correlating at least two of the plurality of analytes based upon similar supportive effects of a particular vitamin/nutrient on the levels of the at least two analytes and selecting the group of vitamins/nutrients based upon the comparison of the patient analyte level set to the plurality of vitamin/nutrient records and the correlation of the at least two plurality of analytes.

* * * * *